US011607568B2

(12) United States Patent
Warnking et al.

(10) Patent No.: US 11,607,568 B2
(45) Date of Patent: Mar. 21, 2023

(54) METHOD AND APPARATUS FOR PULMONARY INTERVENTIONS

(71) Applicant: AerWave Medical, Inc., Naples, FL (US)

(72) Inventors: Reinhard J. Warnking, Westlake, FL (US); Satoshi Nishiaoki, Centereach, NY (US)

(73) Assignee: AERWAVE MEDICAL, INC., Naples, FL (US)

( * ) Notice: Subject to any disclaimer, the term of this patent is extended or adjusted under 35 U.S.C. 154(b) by 0 days.

(21) Appl. No.: 17/350,848

(22) Filed: Jun. 17, 2021

(65) Prior Publication Data

US 2021/0316161 A1     Oct. 14, 2021

Related U.S. Application Data

(63) Continuation-in-part of application No. PCT/US2021/015825, filed on Jan. 29, 2021.
(Continued)

(51) Int. Cl.
*A61N 7/00* (2006.01)
*A61B 8/12* (2006.01)
(Continued)

(52) U.S. Cl.
CPC .............. *A61N 7/00* (2013.01); *A61B 8/085* (2013.01); *A61B 8/12* (2013.01); *A61B 1/00082* (2013.01);
(Continued)

(58) Field of Classification Search
CPC .............. A61N 7/00; A61N 2007/0004; A61N 2007/0043; A61N 2007/0052;
(Continued)

(56) References Cited

U.S. PATENT DOCUMENTS 6,984,993 B2     1/2006  Ariav
2011/0257523 A1  10/2011 Hastings et al.
(Continued)

FOREIGN PATENT DOCUMENTS

WO     WO 2007/009118 A2    1/2007
WO     WO 2011/053757 A1    5/2011
(Continued)

*Primary Examiner* — Hien N Nguyen
(74) *Attorney, Agent, or Firm* — R. Neil Sudol; Henry D. Coleman

(57) ABSTRACT

Apparatus and methods for deactivating bronchial nerves extending along the secondary bronchial branches of a mammalian subject to treat asthma and related conditions. An ultrasonic transducer (11) is inserted into the bronchus as, for example, by advancing the distal end of a catheter (10) bearing the transducer into the secondary bronchial section to be treated. The ultrasonic transducer emits circumferential ultrasound so as to heat tissues throughout circular impact volume (13) as, for example, at least about 1 cm³ encompassing the bronchus to a temperature sufficient to inactivate nerve conduction but insufficient to cause rapid ablation or necrosis of the tissues. The treatment can be performed without locating or focusing on individual bronchial nerves. The apparatus and methods utilized for lung tumor ablation.

6 Claims, 8 Drawing Sheets

Related U.S. Application Data

(60) Provisional application No. 63/002,555, filed on Mar. 31, 2020.

(51) Int. Cl.
*A61B 8/08* (2006.01)
*A61B 1/00* (2006.01)

(52) U.S. Cl.
CPC ............... *A61N 2007/0004* (2013.01); *A61N 2007/0043* (2013.01); *A61N 2007/0052* (2013.01)

(58) Field of Classification Search
CPC .......... A61N 7/022; A61B 8/085; A61B 8/12; A61B 1/00082; A61B 8/445; A61B 34/73; A61B 2018/00541
See application file for complete search history.

(56) References Cited

U.S. PATENT DOCUMENTS

| | | | |
|---|---|---|---|
| 2012/0143099 A1* | 6/2012 | Daniels | A61B 18/1492 601/2 |
| 2013/0197555 A1 | 8/2013 | Schaer | |
| 2013/0281889 A1 | 10/2013 | Gertner | |
| 2014/0031727 A1 | 1/2014 | Warnking | |
| 2016/0008636 A1 | 1/2016 | Warnking | |
| 2016/0220851 A1* | 8/2016 | Mayse | A61B 18/04 |
| 2016/0287912 A1* | 10/2016 | Warnking | A61B 8/08 |

FOREIGN PATENT DOCUMENTS

| | | |
|---|---|---|
| WO | WO 2013/048912 A2 | 4/2013 |
| WO | WO 2014/022777 A1 | 2/2014 |
| WO | WO 2015/066424 A1 | 5/2015 |

\* cited by examiner

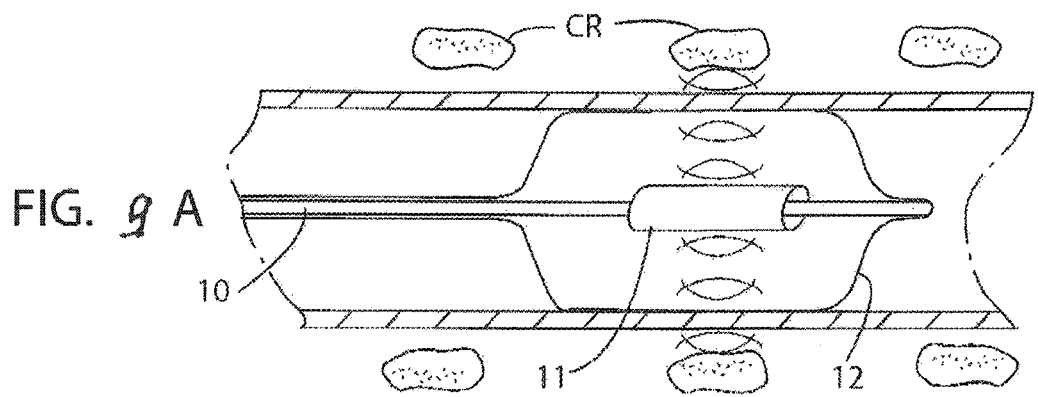
FIG. 9A
FIG. 9B
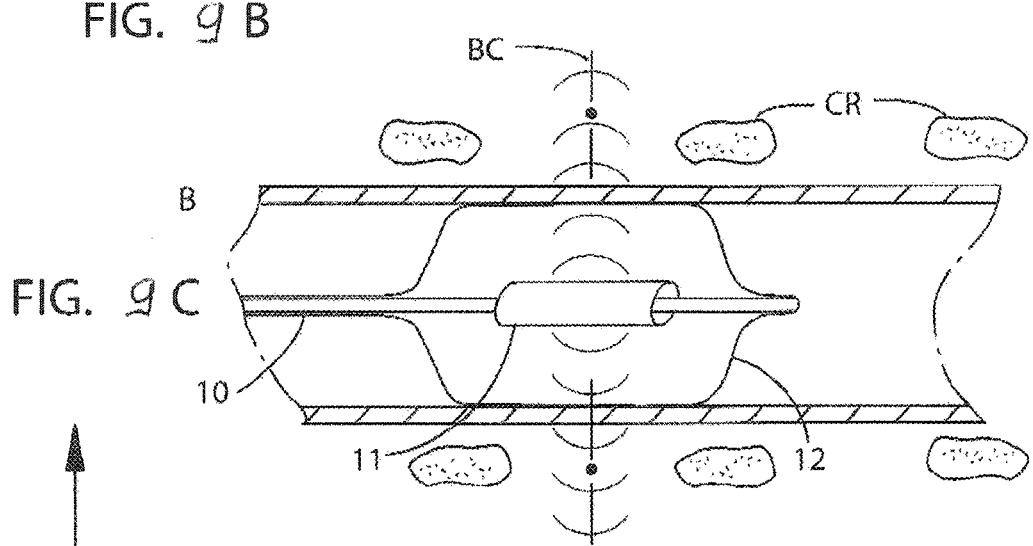
FIG. 9C
FIG. 9D

METHOD AND APPARATUS FOR PULMONARY INTERVENTIONS

CROSS-REFERENCE TO RELATED APPLICATIONS

This application is a continuation-in-part of International Patent Application No. PCT/US2021/015825 filed Jan. 29, 2021. This application claims the benefit of U.S. Provisional Patent Application No. 63/002,555 filed Mar. 31, 2020.

FIELD OF THE INVENTION

The invention relates to an apparatus and an associated method for the treatment of pulmonary disorders. The invention pertains exemplarily to the ablation of lung tumors. The invention also pertains to treatment of asthma and COPD through lung denervation.

BACKGROUND OF THE INVENTION

Lung tumors represent a significant health issue with reduced quality of life due to prolonged and complicated treatment regiments. While procedures to successfully perform tumor-biopsies are established (Electromagnetic Navigation Bronchoscopy, ENB), tumor removal or ablation is being performed in separate procedures putting the patient under enormous psychological stress.

For many years ultrasound has been used to enhance cell repair, stimulate the growth of bone cells, enhance delivery of drugs to specific tissues, and to image tissue within the body. In addition, high-intensity focused ultrasound has been used to heat and ablate tumors and tissue within the body. Ablation of tissue has been performed nearly exclusively by high-intensity focused ultrasound because the emitted ultrasound energy is focused on a specific location to allow in-depth tissue necrosis. However, surrounding tissue and intervening structures that the ultrasound energy must pass through are often exposed to significant energy levels causing collateral damage.

How to selectively target, predominantly lung tumor tissue, without affecting the surrounding tissue by ablating the tumor from its inside is not taught in the prior art. There is a need for a device and method to selectively ablate lung tumor tissue without the risk of causing damage to intervening structures and surrounding tissues. If this can be achieved, treatments would be much easier and faster to perform. Today's multiple diagnostic and therapeutic procedures could be reduced to a one-time diagnosis/treatment, much better tolerated by patients.

Successful treatment of pulmonary diseases such as asthma and COPD are important since these diseases represent a significant global health issue with reduced quality of life. While drug therapy (Bronchodilators, Anti Inflammatories and Leukotrines Modifiers) can be used to treat asthma, it is not always successful and is very expensive. Asthma is a disorder characterized by airway constriction and inflammation resulting in breathing difficulties. Wheezing, shortness of breath and coughing are typical symptoms. These symptoms are caused by increased mucus production, airway inflammation and smooth muscle contraction resulting in airway obstruction. This obstruction can be treated by injuring and scaring the bronchial walls. This remodeling of the bronchial walls stiffens the bronchia and reduces contractility. Mechanical means and heat application have been proposed, as set forth in U.S. Pat. No. 8,267,094. Other approaches focus on destruction of smooth muscle cells surrounding the bronchia as described in US Patent Application Publication No. 2012/0143099A1 and U.S. Pat. No. 7,906,124. European Patent No. 2405841 describes applications of heat shocks through infused agents. Other techniques include applying RF energy to the bronchial wall and thereby directly widening the bronchia through a process which is not disclosed as in U.S. Pat. Nos. 7,740,017 and 8,161,978. Whatever the process, the bronchial wall will be damaged, and the procedure therefore has to be staged as described in U.S. Pat. No. 7,740,017.

Inactivating conduction of nerves surrounding the bronchia by mechanical action, i.e., puncturing, tearing, cutting nerve tissue, has been proposed in US Patent Application Publication No 2012/0203216. In US Patent Application Publication No. 2011/0000118 nerve tissue ablation occurs by applying energy (RF, HIFU, microwave, radiation and thermal energy) directly to the nerves percutaneously. It is not taught how to identify the nerve location in order to align the energy focal point (e.g. HIFU) with the nerve location. This is an issue since nerves are too small to be visualized with standard ultrasound, CT or MRI imaging methods. Therefore, the focal point of the energy field cannot be predictably aligned with the target or nerve location. U.S. Pat. No. 8,088,127 teaches to denervate by applying RF energy to the bronchial wall with the catheter positioned inside the main bronchial lumen. This is a time intensive treatment approach since the RF ablation is limited to the electrode contact area. Therefore, numerous ablation zones need to be pieced together to obtain a larger ablation zone with increased probability of affecting nerves. Efficacy might be severely limited due to the cooling action. In addition, by performing this RF ablation in the main bronchi safety measures need to be implemented to protect the esophagus and peri esophageal vagus nerves. Typically, ablation in the main bronchi requires fluoroscopic imaging and introduction of an esophageal protection/detection balloon to monitor the distance of the esophagus from the treatment site in the main bronchi. There is a need for a device and method to selectively ablate bronchial nerves without the potential of causing damage to bronchial walls and surrounding structures like peri esophageal vagus nerves. This can be achieved, by performing the denervation in the secondary bronchi instead of the main bronchi. This makes the treatments much easier to perform not requiring fluoroscopic imaging or ultrasound measurements to determine esophageal distance from the main bronchial treatment site.

In US Patent Application Publication No. 2016 220851 mechanical means and overlapping ultrasound beams are proposed to seat the ultrasound source, so ultrasound energy is applied between or behind cartilage rings. Except for the mechanical seating no apparatus or method is taught as to how ensure optimal inter cartilage positioning. There is a need for a device and method to easily ensure energy source positioning between cartilage rings. It would be desirable to know whether the ultrasound treatment volume is actually deployed between cartilage rings in particular in secondary bronchi with wider cartilage gaps, or whether the ultrasound is reflected by cartilage rings. Also, enablement of complete circumferential ultrasound transmission with diameter dependent dose optimization is necessary for successful performance of ultrasound lung denervation.

SUMMARY OF THE INVENTION

The present invention is directed in part to the ablation of lung tumors as part of a transbronchial biopsy procedure with 3D navigation such as Electromagnetic Navigation Bronchoscopy (ENB) and optionally in conjunction with the treatment of asthma and COPD through lung denervation. The invention contemplates the use of a circumferential ultrasound field optimized based on analysis of volumetric A mode signals to ensure balloon-tissue coupling, optimal dosing and inter cartilage positioning.

For lung denervation the present invention contemplates selective ablation of bronchial nerves to treat asthma and COPD without causing damage to bronchial walls and surrounding structures including peri esophageal vagus nerves. Pursuant to the invention, the denervation is performed in the secondary bronchi instead of the main bronchi. This makes the treatments much easier to perform insofar as not requiring fluoroscopic imaging or ultrasound measurements to determine esophageal distance from the main bronchial treatment site.

Typically, ablation in the main bronchi requires fluoroscopic imaging and introduction of an esophageal protection/detection balloon to monitor the distance of the esophagus from the treatment site in the main bronchi. Instead of fluoroscopic imaging a distance measurement with ultrasound A mode signals can be utilized. Whatever method of distance measurement is employed the procedure is complicated and often nerve ablation cannot be performed in both the left and right main bronchus at all when a safe treatment distance from esophageal vagus nerves cannot be accomplished. In these cases ablation energy needs to be reduced or the ablation cannot be performed at all so that the lung denervation is only one sided.

The invention provides apparatus for ablating lung tumors and apparatus for ablating nerves around secondary bronchi in a human or non-human mammalian subject. The apparatus according to the invention preferably includes an ultrasound transducer adapted for insertion into a target tumor or into the bronchi of the mammalian subject. By ablating the tumor from the inside out the impact volume or ablation zone is much better controlled than in extracorporeal or endo bronchial, side-firing, ultrasound applications. See, for example, Endobronchial High Intensity Ultrasound for Thermal Therapy of Pulmonary Malignancies, Int'l J of Hyperthermia; Vol 36, Issue 1. The ultrasound transducer desirably is arranged to transmit a ring of ultrasound energy effective to treat tissue in an approximately toroidal or cylindrical impact zone. The apparatus according to this aspect of the invention desirably also includes an actuator which is electrically connected to the transducer. The actuator most preferably is adapted to control the ultrasound transducer to transmit ultrasound energy into an impact zone having a volume of at least approximately 1 $cm^3$, surrounding the catheter so that the circumferentially emitted ultrasound energy is applied at a therapeutic level sufficient to ablate tumor tissue or to inactivate nerve conduction. Tumor dimensions are recorded during pre-procedural CT scans and determine the ultrasound settings (frequency, power and time) as well as the transducer length or focal depth. Typical activation parameters are 1 to several MHz at 10 to 30 W for 1 to several minutes for tumor ablation and several MHz exemplarily 10 MHz at 10 to 20 W for 10 to 30 sec for nerve ablation. The transducer length is either adjusted electronically by selecting a certain number of cylindrical transducer subsegments or through catheter exchange. Further the present invention contemplates use of a separate imaging catheter to ensure complete tumor ablation (for example a commercial IVUS catheter), advanced over the guide wire after the therapy catheter has been withdrawn. Catheter length markings may be provided on both the therapy catheter and the imaging or diagnostic catheter to enable a quick catheter exchange.

The treatment apparatus may more particularly include a catheter with a distal end and a proximal end, the transducer being mounted to the catheter adjacent the distal end, the transducer being disposed inside a balloon which will make contact with the tumor tissue or bronchial wall. This balloon is filled with a circulating cooling fluid to conduct ultrasound energy from the transducer to the tumor tissue or bronchial wall. This cooling fluid also transports excessive heat away from the transducer and the patient's proximate tissues such as the bronchial epithelium in the case of nerve deactivation or ablation of a tumor proximate a bronchial tube. About half of the electrical energy supplied to the transducer is converted into heat while the other half is converted to ultrasonic energy. To be enabled for clinical use, the energy levels and balloon diameters must be adjusted in accordance with the tumor or bronchial dimensions. If these parameters are not properly adjusted (e.g., if there is a constant energy setting for all tumor or bronchial diameters), there is a significant risk of either too much damage caused by the ultrasound ablation or not enough energy to properly ablate the tumor or denervate the lung. Therefore, in order to work with a range of tumor volumes and bronchial diameters the device must be enabled to adjust ultrasound power settings based upon the diameter of the tumor or bronchus at a certain axial penetration. Furthermore, if the balloon's expanded diameter is insufficiently large for the balloon to circumferentially contact the bronchus, the energy will not be delivered circumferentially into the bronchial wall and the denervation or tumor ablation will be incomplete. Therefore, the device must also be enabled to detect whether circumferential contact of balloon with surrounding tissue is complete or partial.

The transducer may be configured to transmit the ultrasound energy in a 360° cylindrical pattern surrounding a longitudinal transducer axis. The transducer also can be subdivided into cylindrical sections which allows for electronic inter cartilage positioning for denervation in secondary bronchi and near field (L L/lambda) adjustment by varying the overall transducer length L according to tumor dimensions.

The system circulating the coupling/cooling fluid may include programmed or hard-wired computational circuitry configured to measure the fluid volume V and pressure P within the balloon and therewith determine balloon contact with the tumor or bronchus. Once the balloon is in circumferential contact with the bronchus or tumor, the system will detect a pressure increase P without a significant volume increase V which is caused by, and indicates, circumferential balloon/tissue contact.

Because the impact volume is relatively large, and because the tissues throughout the impact volume preferably reach temperatures sufficient to necrose tissue, tumor dimensions need to be known from pre procedural CAT or MRI scans and/or imaging catheters exchanged over the wire (OTW) for the therapeutic catheter in order to adjust energy settings and transducer length L according to treatment volume.

An alternative is a rotating single crystal or annular array transducer as used in mechanical IVUS systems (i.e. BSX). Therapeutic ultrasound pulses and/or full rotations could be interleaved with imaging pulses or full rotations to generate quasi simultaneous imaging and therapy modes. When an annular array transducer is utilized very high-resolution images can be obtained. For tumor and or nerve ablation it is advisable to defocus the therapeutic annular array beam to a certain degree in order to avoid harmful energy densities in the focal zone and to ensure sufficiently large treatment volumes in order to maximize efficacy.

As indicated above, placement of a treatment catheter in main bronchi has to ensure sufficient distance from the esophagus and periesophageal vagus nerves. Adequate spacing can be assured by monitoring the distance of a marker balloon inside the esophagus or by fluoroscopic imaging of marker and treatment balloons. Different individuals have different esophageal locations relative to the main bronchi so that distance measurements made either fluoroscopically or through ultrasound A mode analysis are required in every individual treated. Furthermore, when denervation is performed in the main bronchi, tightly spaced cartilage rings present an obstacle in particular for ultrasound ablation. Inasmuch as the cartilage coverage is less dense in the secondary bronchi, introduction and activation of a treatment transducer located in the secondary bronchi is advantageous, both with respect to avoiding damage to the esophagus, but also with respect to facilitating effective ultrasound transmission in the body of the patient by placing the treatment volume between cartilage rings. Otherwise, ultrasound is uselessly reflected by cartilage rings causing damage to the bronchial mucosa. Also, enablement of complete circumferential coupling and therewith ultrasound transmission with diameter dependent dose optimization are part of the invention.

Further aspects of the invention provide probes which can be used in the method and apparatus discussed above, and apparatus incorporating means for performing the steps of the methods discussed above.

BRIEF DESCRIPTION OF THE DRAWINGS

FIGS. 9A and 9C are cross sectional views of a bronchus with an inserted ultrasound catheter with longitudinal position sensing and position optimization, showing the catheter and particularly an ultrasound transducer and balloon at different longitudinal positions in the bronchus, relative to cartilage rings thereof.

FIGS. 9B and 9D show volume integrated A mode signals for balloon positioning relative to cartilage rings

DETAILED DESCRIPTION

Figure 2:
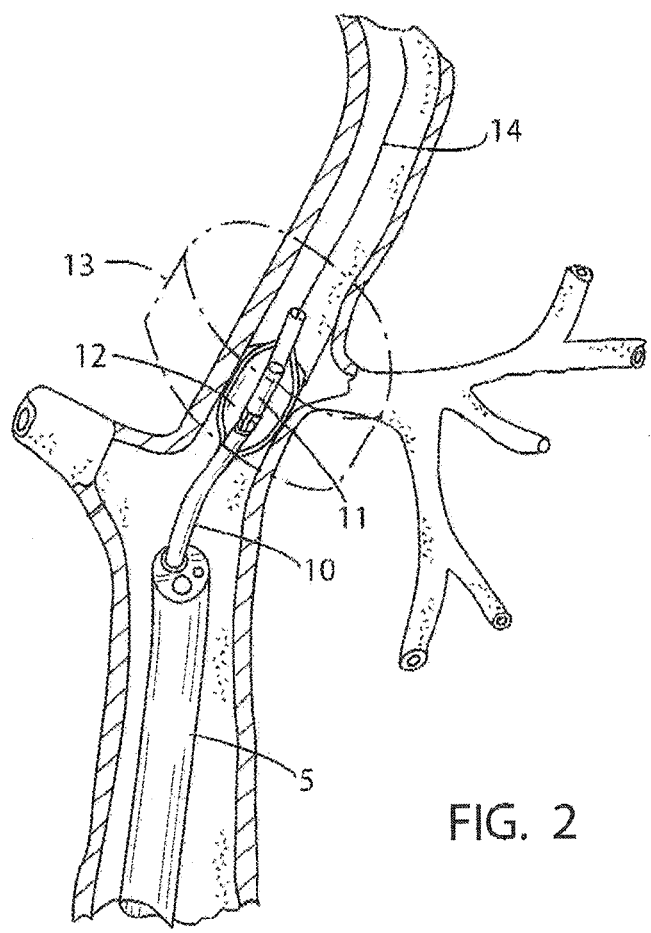
FIG. 2 is partially a side elevational view of a treatment catheter 10 advanced through a bronchoscope 5 into a bronchial branch and a bronchial sectional view, diagrammatically depicting an ultrasound treatment volume 13.
Figure 3:
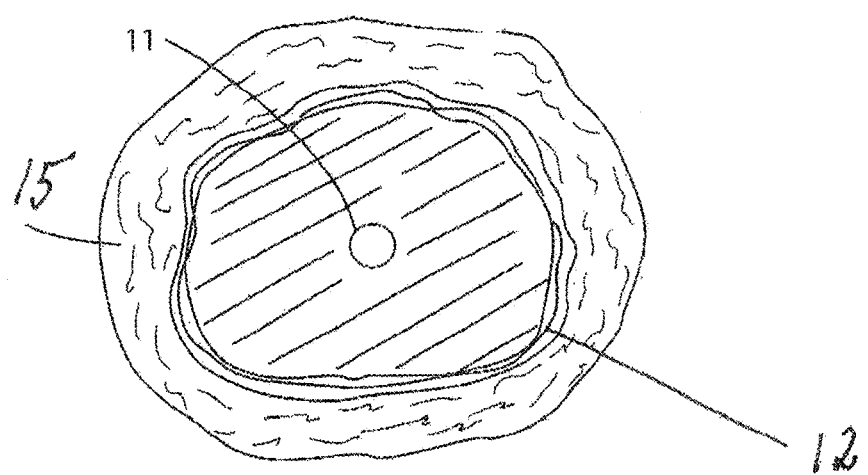
FIG. 3 is a schematic transverse cross sectional view through a tumor 15 with an ultrasound transducer 11 in the center surrounded by cooling fluid in a balloon 12.
Figure 4:
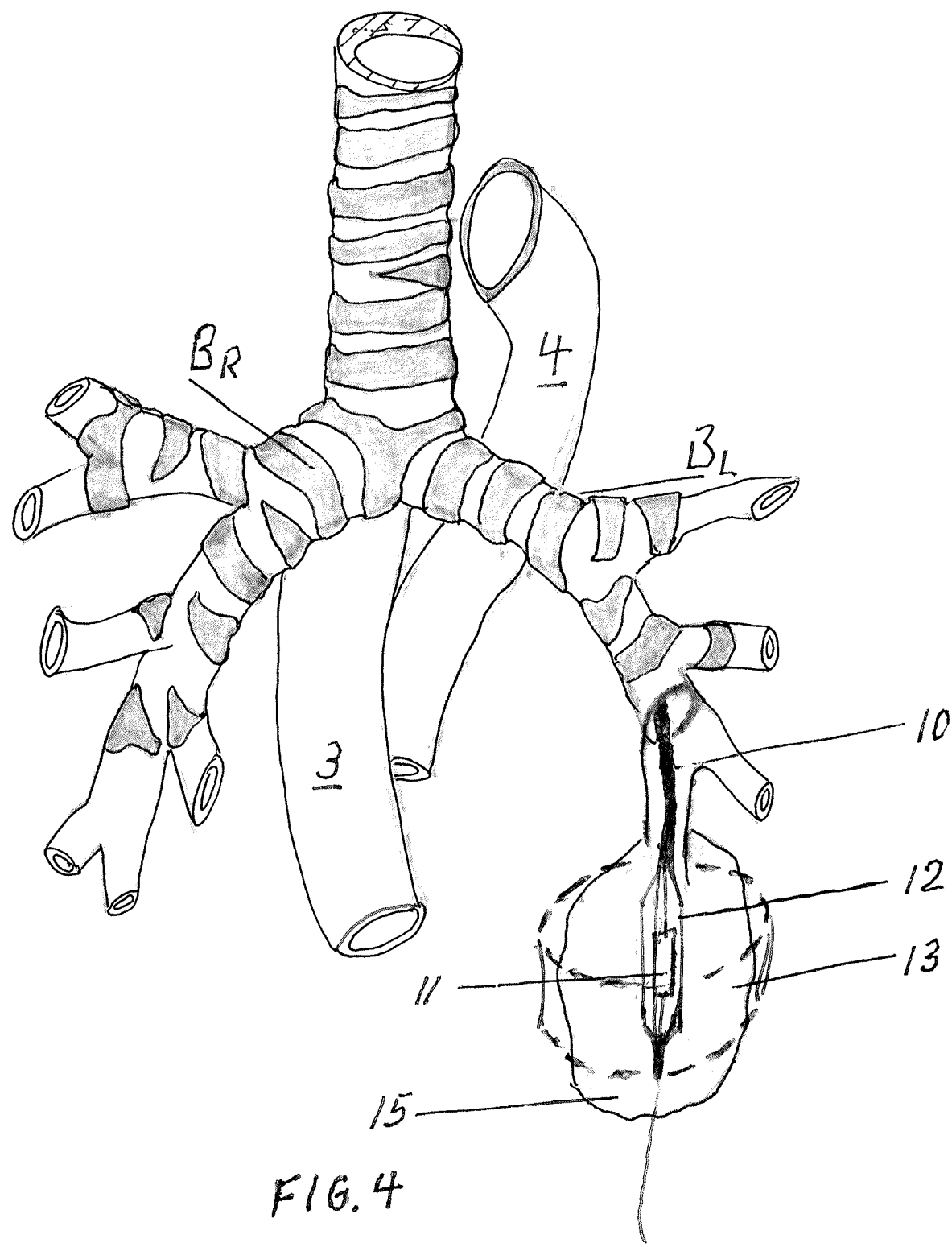
FIG. 4 is a partially anatomical view showing the ablation catheter 10 advanced through the left bronchus $B_L$ into a tumor 15 over a guide wire 14 placed during electromagnetic navigation bronchoscopy (ENB).

Apparatus according to one embodiment of the invention is advanced through the working channel of a bronchoscope 5 in FIG. 2. Alternatively, an ultrasound catheter 10 can be advanced through a sheath or directly without any delivery instrument over a guide wire 14 which has been placed by electromagnetic navigation bronchoscopy (ENB). The sheath or ultrasound catheter 10, generally, may be in the form of an elongated tube having a proximal end, a distal end and a proximal-to-distal axis. As used in this disclosure with reference to elongated elements for insertion into the body, the term "distal" refers to the end which is inserted into the body first, i.e., the leading end during advancement of the element into the body, whereas the term "proximal" refers to the opposite end. The sheath or ultrasound catheter may be a steerable sheath or catheter. Thus, the sheath or catheter may include known elements such as one or more pull wires (not shown) extending between the proximal and distal ends of the sheath or catheter and connected to a steering control arranged so that actuation of the steering control by the operator flexes the distal end of the sheath or catheter in a direction transverse to the axis. The sheath or the ultrasound catheter 10 may be inserted into a tumor which has been traversed by a guide wire placed under a 3D guided trans bronchial biopsy procedure (ENB) as shown in FIG. 4. Catheter 10 has compliant balloon 12 mounted at the distal end. In its inflated condition (FIGS. 2 and 3), balloon 12 engages the tumor/bronchial wall and therewith allows for ultrasound to be conducted from transducer 11 into surrounding tumor/bronchial tissues 15 (FIGS. 4 and 3).

Figure 10:
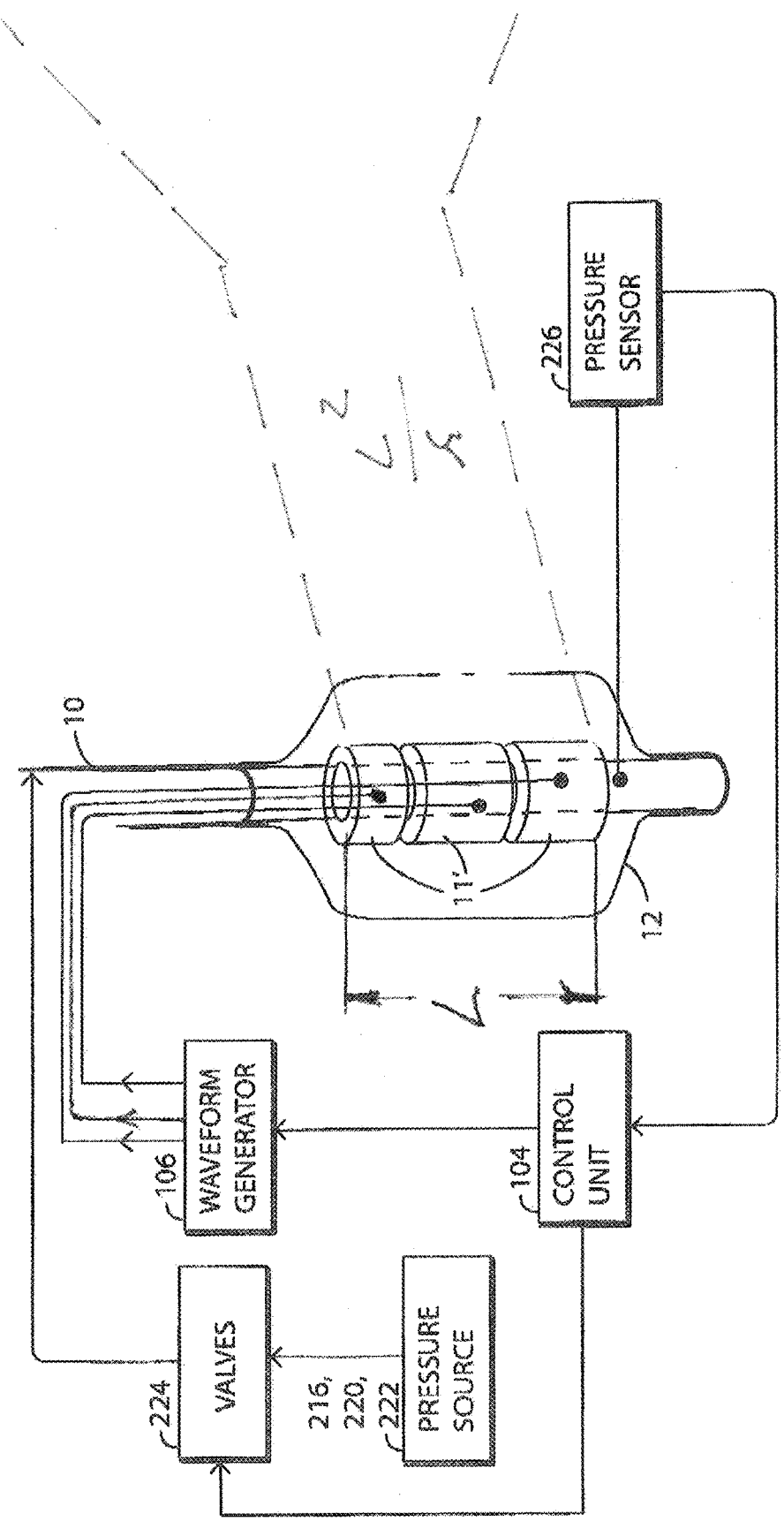
FIG. 10 shows a subdivided transducer to allow for electronic inter-cartilage positioning and transducer length adjustment L for varying the near field zone to adjust tumor treatment volumes.

Ultrasound transducer 11 (FIG. 2) is mounted adjacent the distal end of catheter 10 within balloon 12. Transducer 11, which is desirably formed from a ceramic piezoelectric material, is of a tubular shape and has an exterior emitting surface in the form of a cylindrical surface of revolution about the proximal-to-distal axis of the transducer 11. The transducer 11 typically has an axial length of approximately 2 and approximately 10 mm, and preferably about 6 mm. As shown in FIG. 10 this length L can be varied electronically to adjust the near field zone to accommodate different treatment depths and therewith tumor volumes. Also, the axial position of the treatment volume can be varied electronically by selectively activating different sub elements 11' to allow for inter cartilage positioning of the treatment volume for denervation in the secondary bronchi or treatment of tumors proximate to or surrounding cartilage covered bronchial sections. The outer diameter of the transducer 11 is approximately 1.5-3 mm in diameter, and preferably 2 mm. The transducer 11 also has electrically conductive coatings (not shown) on its interior and exterior surfaces. Thus, the transducer may be physically mounted to the catheter 10. The coatings are electrically connected to ground and signal wires. Wires 110 extend from the transducer 11 through a lumen in the catheter 10 to a connector 102 electrically coupled with the ultrasound control system. The lumen (not designated) extends between the proximal end and the distal end of catheter 10, while the wires 110 extend from the transducer 11, through the lumen, to the proximal end of the catheter 10.

Transducer 11 is arranged so that ultrasonic energy generated in the transducer is emitted principally from the exterior or outer surface (not separately designated). Thus, the transducer may include features arranged to reflect ultrasonic energy directed toward the interior of the transducer so that the reflected energy, travelling outwardly, reinforces the ultrasonic vibrations at the exterior surface. For example, transducer 11 may be configured with air backing to reflect energy at an interior surface of the transducer 11 and thereby redirected the energy outwardly to enhance the overall efficiency of the transducer.

Transducer 11 is also arranged to convert ultrasonic waves impinging on the exterior surface into electrical signals on wires 110. While A-mode signals integrated over the treatment volume cannot provide for spatial resolution like with a 2D imaging transducer, a conclusion about the bronchial lumen can be made based on the magnitude of the amplitude and distance (time) of the volume-integrated A-mode signal as shown in an oscilloscope screen shot in FIG. 7C. Stated another way, transducer 11 can act either as an ultrasonic emitter or an ultrasonic receiver. The receiving mode is of particular importance for an array type transducer as described in U.S. patent application Ser. No. 14/770,941, Publication No. 2016/0008636, because with an array type transducer 11 the received echoes can be electronically focused, using phased array processing, and high-resolution images can be achieved.

The transducer 11 is designed to operate, for example, at a frequency of approximately 1 MHz to approximately a few tens of MHz, and typically at approximately 10 MHz for denervation and 1 to 5 MHz for tumor ablation. The actual frequency of the transducer 11 typically varies somewhat depending on manufacturing tolerances. The optimum actuation frequency of the transducer may be encoded in a machine-readable or human-readable element (not shown) such as a digital memory, bar code or the like affixed to the catheter. Alternatively, the readable element may encode a serial number or other information identifying the individual catheter, so that the optimum actuation frequency may be retrieved from a central database accessible through a communication link such as the internet.

Figure 1:
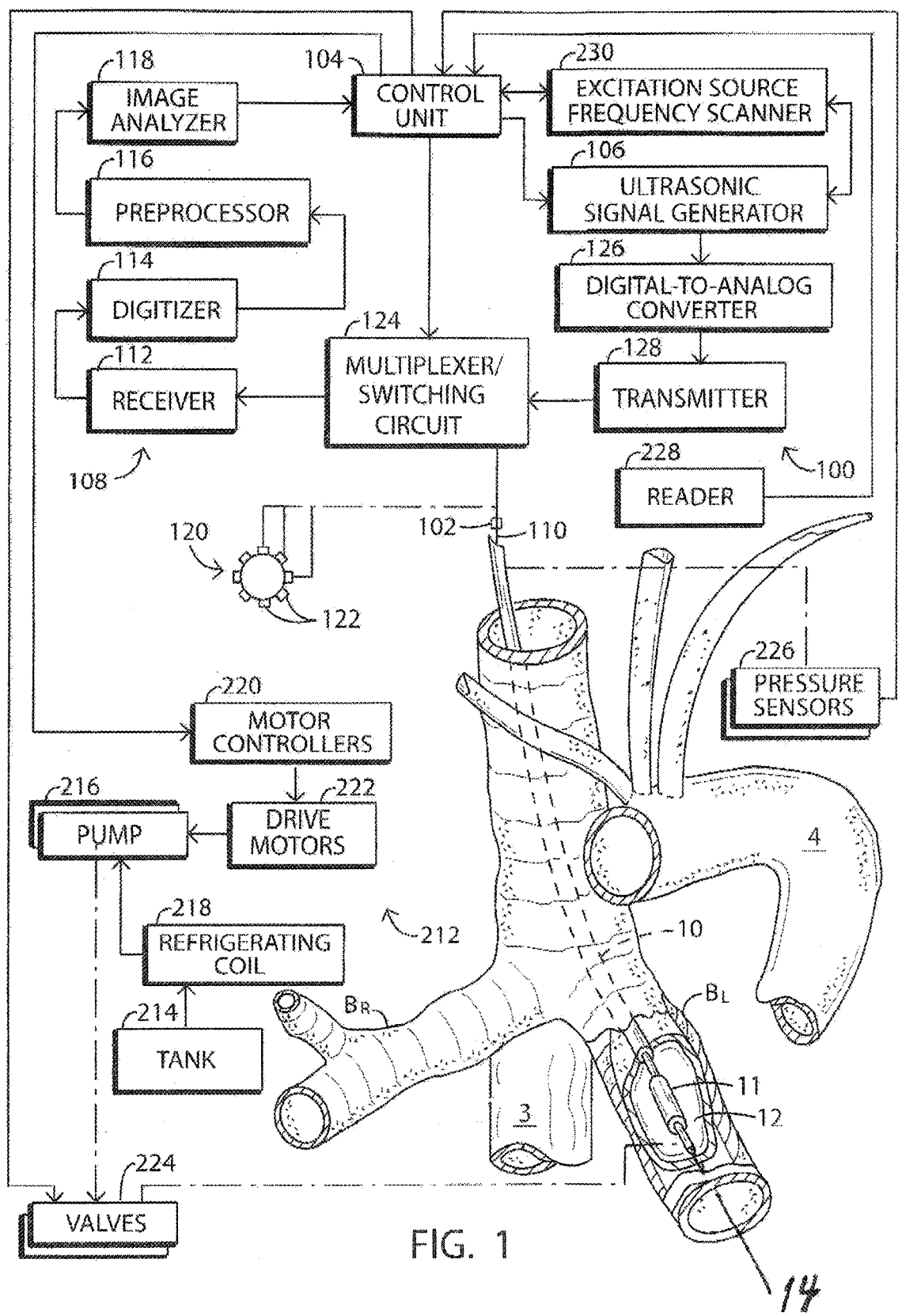
FIG. 1 is partially an anatomical view of typical main bronchial trunks $B_L$ and $B_R$ and associated structures and partially a block diagram of a system for treatment of pulmonary conditions, in accordance with the present invention.

An ultrasound control system, also referred to herein as an actuator, is releasably connected to catheter 10 and transducer 11 through a plug connector 102 (FIG. 1). A control unit 104 and an ultrasonic signal or waveform generator 106 are arranged to vary or adjust the amplitude and timing of the electrical signals to control the power level and duration of the ultrasound-frequency signals emitted by transducer 11. An energization circuit 100 including control unit 104 and ultrasonic signal generator 106 also includes a detection subcircuit 108 arranged to detect electrical signals generated by transducer 11 and transmitted via wires 110 and communicate such signals to the control unit 104. More particularly, detection subcircuit 108 includes a receiver or echo signal extractor 112, a digitizer 114, an ultrasonic echo signal preprocessor 116, and an image analyzer 118 connected in series to one another. Ultrasonic signal generator 106 produces both therapeutic denervation or tumor ablation signals and outgoing diagnostic A mode signals. As discussed hereinafter, the outgoing diagnostic signals and the returning echo signals may be transmitted and picked up by transducer 11. A multiplexer or switching circuit 124 is operated by control unit 104 to switch to a receiving mode after diagnostic signals are emitted during a transmitting mode via a digital-to-analog converter 126 and a transmitter module 128.

As depicted in FIG. 1, a circulation device 212 is connected to lumens (not shown) within catheter 10 which in turn are connected to balloon 12. The circulation device 212 is arranged to circulate a liquid, preferably an aqueous liquid, through the catheter 10 to the transducer 11 in the balloon 12. The circulation device 212 may include elements such as a tank 214 for holding the circulating coolant, pumps 216, a refrigerating coil 218, or the like for providing a supply of liquid to the interior space of the balloon 12 at a controlled temperature, desirably at or below body temperature. By lowering the coolant temperature the inner radius of the circumferential treatment volume can be increased in order to protect certain structures like the inner bronchial lining from harmful temperatures. The control unit 104 interfaces with the circulation device 212 to control the flow of fluid into and out of the balloon 12. For example, the control unit 104 may include motor control devices 220 linked to drive motors 222 associated with pumps 216 for controlling the speed of operation of the pumps. Such motor control devices 220 can be used, for example, where the pumps 216 are positive displacement pumps, such as peristaltic pumps. Alternatively, or additionally, the control unit 104 may operate structures such as controllable valves 224 connected in the fluid circuit for varying resistance of the circuit to fluid flow.

Figure 7A:
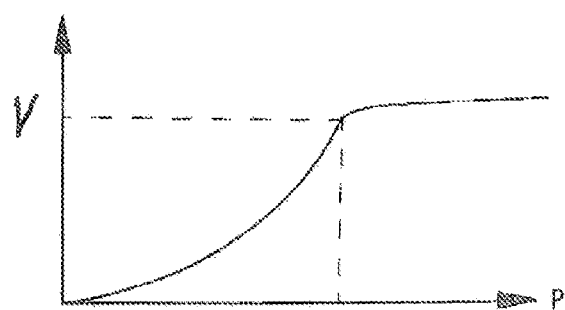
FIG. 7A through 7C show balloon diameter determination through pressure P/volume V monitoring in 7A and ultrasound pinging in 7B with the corresponding screen shot of an ultrasound volumetric A mode signal in 7C

The ultrasound system may further include pressure sensors 226 (FIG. 1), to monitor the liquid flow through the catheter 10 and determine the bronchial diameter and/or circumferential tissue contact as shown in FIG. 7A by detecting the point of pressure increase P without significant volume increase V which corresponds with the balloon reaching full inflation inside the bronchus and making circumferential tissue contact. The corresponding diameter can be determined through a look-up table, for instance, in a memory connected to control unit 104, where volume and pressure values are related to balloon diameters. At least one pressure sensor 226 monitors the flow of the liquid to the distal end of catheter 10 to determine if there is a blockage while another pressure sensor 226 monitors leaks in the catheter 10. While the balloon 12 is in an inflated state, the pressure sensors 226 and 228 maintain a desired pressure in the balloon preferably so that the compliant balloon occludes the bronchus and makes circumferential tissue contact.

The ultrasound system 100 incorporates a reader 228 for reading a machine-readable element on catheter 10 and conveying the information from such element to the control unit or board 104. As discussed above, the machine-readable element on the catheter may include information such as the operating frequency and efficiency of the transducer 11 in a particular catheter 10, and the control unit 104 may use this information to set the appropriate frequency and power for exciting the transducer. Alternatively, the control unit 104 may be arranged to actuate an excitation source or frequency scanner 230 to measure the transducer operating frequency by energizing the transducer at a low power level while scanning the excitation frequency over a pre-determined range of frequencies for example 1 Mhz-11 Mhz and monitoring the response of the transducer 11 to such excitation and to select the optimal operating frequency.

The ultrasonic system may be similar to that disclosed in U.S. patent application Ser. No. 14/770,941, Publication No. 2016/0008636, the disclosure of which is incorporated by reference herein.

After preparation of a human or non-human mammalian subject such as a patient (preparation of the tracheal access site), and connection of the catheter 10 to the ultrasound system, the ultrasound catheter 10 is inserted into the working channel of the bronchoscope after the bronchoscope has been advanced to the desired treatment site under visual guidance through the bronchoscope camera or electromagnetic guidance. Alternatively, a steerable sheath, preferably with ultrasound imaging capability as described in U.S. patent application Ser. No. 14/770,941, Publication No. 2016/0008636, can be used as a delivery channel for the treatment catheter. In another embodiment the treatment catheter is equipped with a steering or deflection mechanism and can be advanced directly to the treatment site as shown in FIG. 1. If the catheter combines imaging and therapeutic capabilities as described in the U.S. patent application Ser. No. 14/770,941, Publication No. 2016/0008636, this delivery method enables the fastest procedure time and is easily tolerated by the patient. Yet another embodiment provides for a guide wire 14 (FIGS. 1-4) to be delivered through the working channel of the bronchoscope to the treatment site and the ultrasound treatment catheter to be advanced over the wire after the bronchoscope has been withdrawn. This technique will allow for very small, flexible bronchoscopes to be utilized.

Once the distal end of the catheter is in position within a secondary bronchial branch or a tumor, pumps bring balloon 12 to an inflated condition as depicted in FIGS. 1 and 2. In this condition, the compliant balloon 12 engages the bronchial wall or tumor, and thus centers transducer 11 within the bronchial branch or tumor, with the axis of the transducer 11 approximately coaxial with the axis of the bronchial branch or tumor. This not only provides for a relatively homogeneous energy distribution circumferentially, but also keeps the very high energy levels close to the transducer located inside the cooling fluid where they are harmless, since ultrasound does not interact with the cooling fluid. If these peak energy levels were allowed to be located close to the bronchial wall, injury would result. Another advantage of proper centering is that the treatment volume coincides with the relatively flat portion of the 1/R curve, providing an almost constant power level throughout the treatment volume.

During treatment, the circulation apparatus, including pump 216, coils 218, and valves 224 (FIG. 1), maintains a flow of cooled aqueous liquid into and out of balloon 12, so, as to cool the transducer 11 and to protect proximal structures like the inner bronchial lining in case of a denervation procedure. The cooled balloon 12 also tends to cool the interior surface of the tumor to prevent excessive ablation temperatures and therewith a blocking effect for distal treatment areas.

Figure 7B:
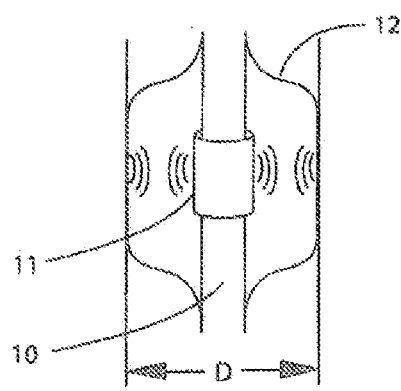
Figure 7C:
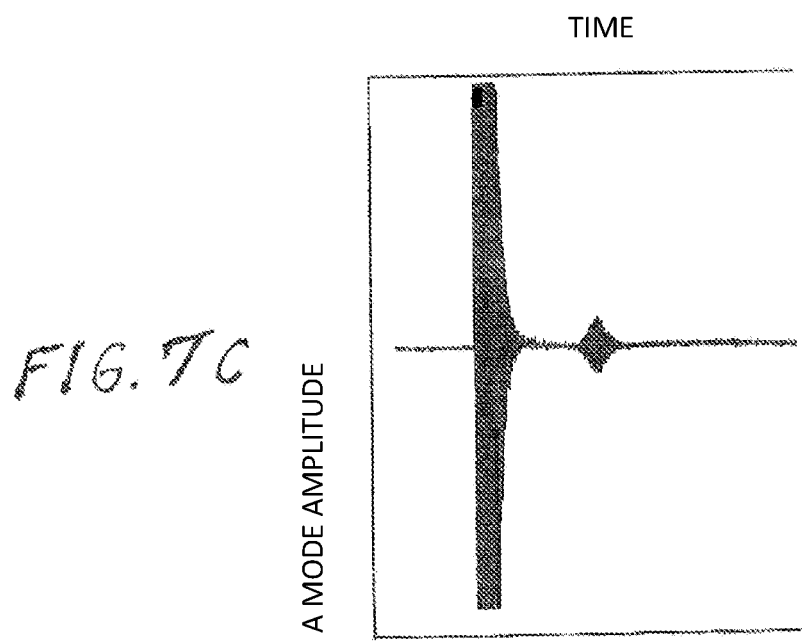

In another embodiment, the ultrasound system uses transducer 11 to measure the size of the bronchus as shown in FIGS. 7B and 7C. The control unit 104 and ultrasound source or ultrasonic signal generator 106 actuate the transducer 11 to "ping" the bronchus with an ultrasound pulse or burst. The ultrasonic waves in this pulse are reflected by the bronchial wall onto transducer 11 as echoes. Transducer 11 converts the echoes to electrical echo-encoding signals as shown in FIG. 7C. The ultrasound system, particularly control unit 104 (which typically takes the form of a programmed general-purpose computer or a hardwired processor), then determines the diameter D of the bronchus by analyzing the echo signals. For example, the ultrasound system may determine the time delay between actuation of the transducer 11 to produce the "ping" and the return of echo signals. The width of the return signal represents the difference between diameter dmax and diameter dmin in case the bronchial section is not perfectly circular but oval shaped. The ultrasound system uses the measured bronchus size D to set the acoustic power to be delivered by transducer 11 during application of therapeutic ultrasonic energy for denervation or tumor ablation. For example, the control board or unit 104 may use a lookup table correlating a particular echo delay (and thus bronchial diameter D) with a particular power level. For tumor ablations the treatment diameters are known from preprocedural CT or MRI imaging or from catheter imaging. Generally, the larger the diameter, the more power should be used. While the integrated A-mode signals over the treatment volume by a cylindrical uniform transducer cannot provide for spatial resolution, a conclusion about reflectors can be made based on the magnitude of the amplitude and distance (time) of the volume-integrated A-mode signal. In other words, the presence of the balloon/tissue interface can be detected but cannot be differentiated circumferentially.

Figure 8:
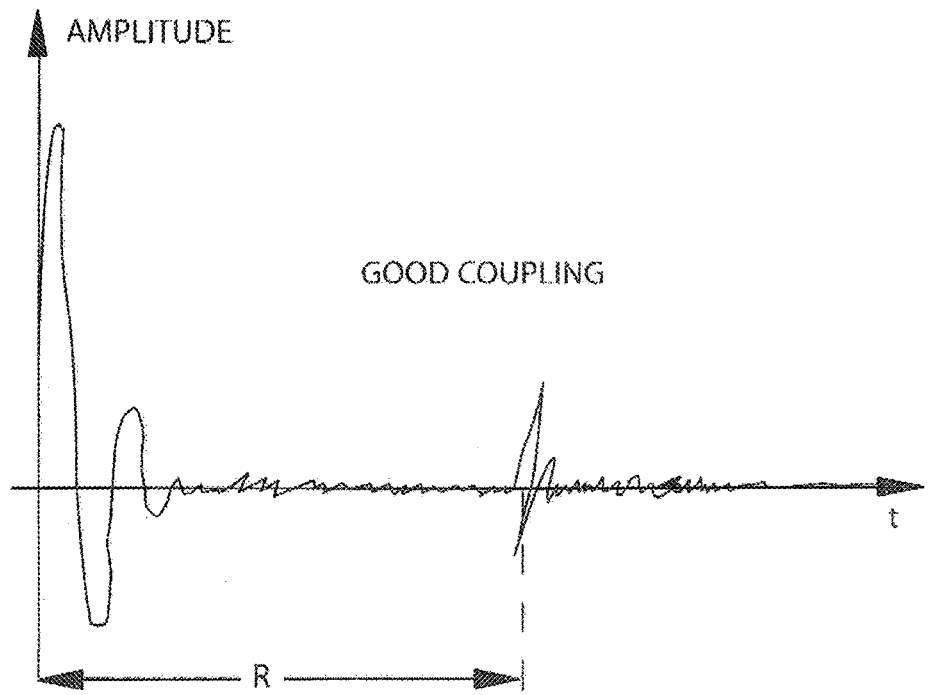
FIGS. 8A and 8B are graphs showing magnitudes of volume integrated A mode signals for complete (8A) and incomplete (8B) balloon-bronchus/tumor coupling.
Figure 8:
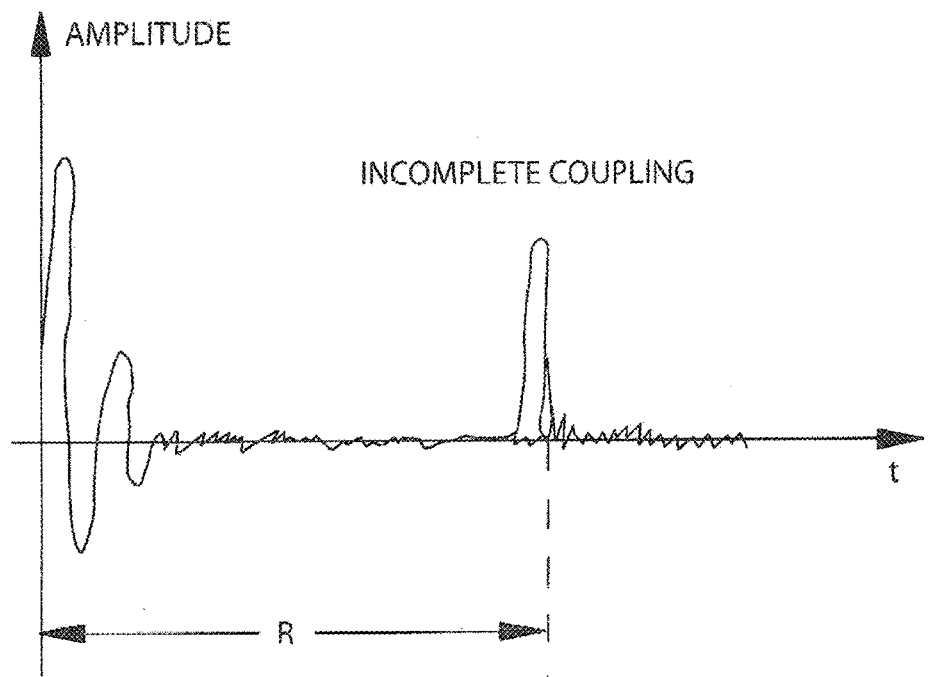

The volume integrated echo will also represent coupling of the balloon with the bronchial wall/tumor tissue as shown in FIGS. 8A and 8B. If air is trapped the echo amplitude of the balloon/bronchus interface will be significantly larger as shown in FIG. 8B than in case of complete circumferential coupling as shown in FIG. 8A. While spatial resolution is not provided by this volume integrated A-mode signal, air pockets, i.e., trapped air, can be clearly detected by analyzing the amplitude of the integrated A-mode signal at the balloon/tissue interface or the corresponding time delay between transmit and receive echo as shown in FIGS. 8A and 8B. While the integrated A-mode signals over the treatment volume cannot provide for spatial resolution, a conclusion about trapped air can be made based on the magnitude of the amplitude and distance (time) of the integrated A-mode signal, see FIGS. 8A and 8B. In other words, the presence of air at the balloon/tissue interface can be detected by analyzing the echo amplitude but the trapped air cannot be located circumferentially. If the balloon diameter is not adjusted properly to eliminate the trapped air, the energy will not be delivered completely circumferentially which will affect the efficacy of the procedure negatively.

For denervation procedures it is preferable to advance the treatment volume distal to the first bronchial bifurcation so that 2 (instead of 1) energy applications are administered on each side. This will simplify the procedure significantly since precautions such as esophageal cooling/location balloon and/or fluoroscopic imaging can be omitted if the procedure is performed in secondary versus main bronchi. In order to explain the difficulties associated with denervation in the main bronchi without causing other damage, the anatomy of the bronchial system and nerves will be described now. FIG. 1 illustrates in part the main bronchi $B_R$ and $B_L$ and the esophagus 3. As can be seen, esophagus 3 and the peri-esophageal left and right vagus nerves (not shown) are in close vicinity to the main bronchi $B_L$ and $B_R$. Therefore, placement of treatment catheter 10 (here shown in the left main bronchus $B_L$) has to ensure sufficient distance from esophagus 3 and periesophageal vagus nerves so that subsequent pulmonary therapy does not damage the esophagus or the vagus nerves. This can be assured by monitoring the distance of a marker balloon inside the esophagus from the ultrasound transducer by ultrasonic A mode measurements or by fluoroscopic imaging of marker and treatment balloons. Different individuals have different esophageal locations relative to the main bronchi $B_R$ and $B_L$ so that distance measurements either fluoroscopically or through ultrasound A mode analysis are required in every individual treated. Furthermore, when denervation is performed in the main bronchi (as shown in FIG. 1 for $B_L$), tightly spaced cartilage rings will represent an obstacle in particular for ultrasound ablation. As shown in FIG. 4 the cartilage coverage is less dense in the secondary bronchi distal to the second bifurcation making this location much better suited for ultrasound denervation.

The volume integrated A-mode signal can also be analyzed to optimize positioning of the energy source or transducer 11 so that the portion of the ultrasound reflected by cartilage rings CR is minimized and the ultrasound treatment volume is positioned in a plane BC mainly between cartilage rings CR. FIG. 9A shows catheter 10, transducer 11 and balloon 12 positioned within a cartilage ring CR, that is, in a transverse plane of the cartilage ring. FIG. 9C depicts catheter 10, transducer 11 and balloon 12 positioned in a transverse plane BC between adjacent cartilage rings CR. Optimized positioning is obtained by analyzing the volume integrated A-mode signal and minimizing a circumferentially integrated cartilage echo Uc by moving the catheter 10, moving the transducer 11 inside the balloon 12 or by electronic selection of transducer sections 11' as shown in FIG. 10. For orientation, echo signal Uc will occur distally to a bronchial wall signal Ub. In other words rather than positioning ultrasound energy sources through mechanical seating mechanisms by forcing the ultrasound source into certain positions relative to cartilage rings, as described in U.S. Patent Application Publication No. 2016/0220851, the positioning is here controlled directly by detecting cartilage echoes and adjusting the longitudinal position of ultrasound source transducer 11 to optimally deliver the ultrasound energy in between cartilage rings CR. The complete catheter 10 may be moved longitudinally until echo signal Uc is minimal or the transducer 11 inside the balloon 12 can be moved until echo signal Uc is minimal. In another embodiment transducer segments 11' or groups thereof are activated until echo signal Uc is minimized and therewith an optimal positioning between cartilage rings CR has been obtained. This inter cartilage positioning is of particular importance and advantage when the treatment is being performed in secondary bronchi since the cartilage spacing is coarse with wider cartilage segments and gaps as in main bronchi. Also, for tumors surrounding proximal bronchial branches this inter cartilage positioning is critical.

The physician initiates the treatment through a user interface (not illustrated). In the treatment, the ultrasonic system or actuator, and particularly the control board or unit 104 and ultrasonic signal source or generator 106, energizes transducer 11 to deliver therapeutically effective ultrasonic waves to a generally toroidal impact zone or volume 13 (FIG. 2). The ultrasound energy transmitted by the transducer 11 propagates generally radially outwardly and away from the transducer 11 encompassing a full circle, or 360° of arc about the proximal-to-distal dimension or longitudinal axis of the transducer 11 and the axis of the bronchial section and/or tumor treated.

The selected operating frequency, focus-characteristic, placement, size, and the shape of the ultrasound transducer 11 allow the entire treatment zone to lie within the "focal field" of the transducer 11. As shown in FIGS. 2 and 10, within this region an outwardly spreading, focused omnidirectional (360°) cylindrical field of ultrasound waves is generated by the transducer 11. For a cylindrical transducer, the radial extent of the near field region, in which the beam can be focused, is defined by the expression $L^2/\lambda$, where L is the axial length of the transducer 11 (see FIG. 10) and $\lambda$ is the wavelength of the ultrasound waves. At distances from the transducer 11 surface greater than $L^2/\lambda$, the beam begins to spread axially to a substantial extent as shown in FIG. 10. However, for distances less than $L^2/\lambda$, the beam does not spread axially to any substantial extent (FIGS. 2 and 10). The impact volume 13 is generally cylindrical and coaxial with the bronchial section and/or tumor treated (FIGS. 2 and 4). The impact volume extends from the balloon exterior or outer surface to an impact radius, where the intensity of the ultrasonic energy is too small to heat the tissue to the temperature range that will cause inactivation of nerves or tumor ablation.

As discussed above, the length of the transducer 11 may vary between 2 mm and 10 mm, but is preferably 6 mm, to provide a wide aperture to enable focusing. The diameter of the transducer 11 may vary between 1.5 mm and 3.0 mm, and is preferably about 2.0 mm.

The power level desirably is selected so that throughout the impact volume, solid tissues are heated to about 65° C. or more which requires sonication times of up to several minutes for tumor ablation and about 50 C for denervation requiring 10 to 30 sec sonication durations. For denervation desirably all of the solid tissues within the treatment volume, including the wall of the bronchus remain well below 65° C. Thus, throughout the impact region, the solid tissues (including all of the bronchial nerves) are brought to a temperature sufficient to inactivate nerve conduction but below that which causes rapid necrosis of the tissues as in tumor ablations.

Research shows that nerve inactivation occurs at much lower temperatures and much faster than tissue necrosis. See Bunch, Jared. T. et al. "Mechanisms of Phrenic Nerve Injury During Radiofrequency Ablation at the Pulmonary Vein Orifice, *Journal of Cardiovascular Electrophysiology*, Volume 16, Issue 12, pg. 1318-1325 (Dec. 8, 2005), incorporated by reference herein. Since, necrosis of tissue typically occurs at temperatures of 65° C. or higher for approximately 10 sec or longer while inactivation of nerves typically occurs when the nerves are at temperatures of 42° C. or higher for several seconds or longer, the dosage of the ultrasound energy is chosen to keep the temperature in the impact volume 13 between those temperatures for several seconds or longer. Operation of the transducer within these treatment parameters thus provides a therapeutic dosage that inactivates nerves without causing damage to the secondary bronchi In addition, the circulation of cooled liquid through the balloon 12 containing the transducer 11 may also help reduce the heat being transferred from the transducer 11 to the inner layer of the bronchus. Hence, the transmitted therapeutic ultrasound energy does not damage the inner layer of the bronchus, providing a safe treatment in case of denervation.

In order to generate the therapeutic dosage of ultrasound energy for nerve inactivation, the acoustic power output of the transducer 11 typically is approximately 10 watts to approximately 100 watts, more typically approximately 10 to approximately 20 watts. The duration of power application typically is approximately 2 seconds to approximately a minute or more, more typically approximately 10 seconds to approximately 30 seconds. The dosage used for tumor ablation (necrosis) varies between 10 to 30 W for up to several minutes. The optimal dosage with a particular system to achieve the desired temperature levels may be determined by mathematical modeling or animal testing.

The impact volume 13 of the ultrasound energy encompasses the entire bronchial section treated and closely surrounding tissues, and hence encompasses all of the bronchial nerves surrounding the secondary bronchi. Therefore, the placement in the bronchus of the transducer 11 may be indiscriminate in order to inactivate conduction of all the surrounding bronchial nerves. As used in this disclosure "indiscriminate" and "indiscriminately" mean without targeting, or locating on, any specific bronchial nerves. For nerve ablation performed in particular in the secondary bronchi or for ablation of tumors located in proximal lung sections, the ultrasound source position will be optimized to lay between cartilage rings as described above with reference to FIGS. 9A to 9D.

Numerous variations and combinations of the features discussed above can be utilized. For example, the ultrasound system may control the transducer 11 to transmit ultrasound energy in a pulsed function during application of therapeutic ultrasonic energy. The pulsed function causes the ultrasound transducer 11 to emit the ultrasound energy at a duty cycle of, for example, 50%. Pulse modulation of the ultrasound energy is helpful in limiting the tissue temperature while increasing treatment times which will result in a more homogenous or even temperature distribution throughout the treatment volume.

The pulsed therapeutic function can also be designed to cause electrophoresis and enhance drug delivery to treat a lung tumor by causing cavitation which produces pressure waves to permeabilize cell membranes. This way non thermal ultrasound energy is used for targeting or controlling drug release through 2 mechanisms: Causing cell membranes to become more permeable to drugs and to disrupt the structure of the drug carrier vehicle to release the drug. These cavitation effects are possibly also advantageous for nerve ablation and to stimulate new cell creation to replace diseased cells in COVID affected lung segments.

The pulsed therapeutic function can also be interleaved with a diagnostic imaging mode when the ultrasound transducer comprises an array of separately activatable transducer elements instead of a single unitary cylindrical transducer. This way diagnostic ultrasound imaging can be obtained essentially or quasi simultaneously with the therapeutic treatment, see U.S. patent application Ser. No. 14/770,941, Publication No. 2016/0008636.

In a further variant, the balloon 12 may be formed from a porous membrane or include holes, such that cooled liquid circulated within the balloon may escape or flow from the balloon 12 against the bronchial walls or tumor tissue to improve acoustic contact and enable axial catheter movement for inter-cartilage positioning.

Typically, catheter 10 is a disposable, single-use device. The catheter 10 or ultrasonic system may contain a safety device that inhibits the reuse of the catheter 10 after a single use. Such safety devices per se are known in the art.

In yet another variant, the catheter 10 itself may include a steering mechanism which allows the physician to directly steer the distal end of the catheter. In this case a bronchoscope or sheath may be omitted.

Figure 5:
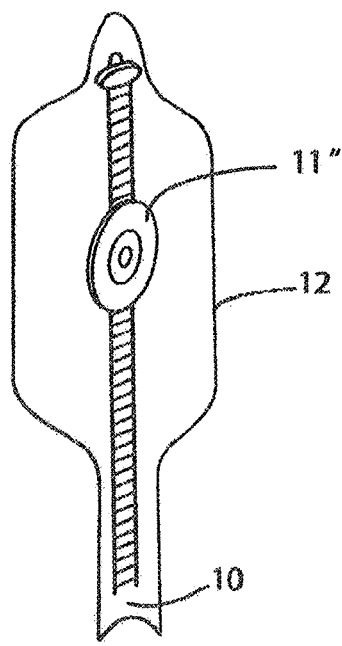
FIG. 5 is a schematic cross-sectional view of a rotational ablation/imaging catheter in accordance with the invention

As depicted in FIG. 5, a rotating transducer 11" as found in mechanical intravascular ultrasound (IVUS) system (e.g., of Boston Scientific, BSX) may be utilized. Therapeutic ultrasound pulses may be interleaved with imaging pulses to generate quasi simultaneous imaging/therapy modes.

The system (FIG. 1) circulating the coupling/cooling fluid may be configured to measure the fluid volume V and pressure P and therewith determine the bronchial diameter (FIG. 7A). Based on the measured bronchial diameter, the overall ultrasound power can be automatically optimized for denervation procedures. For tumor ablation the dosage will be calculated based on pre procedural images.

Figure 6:
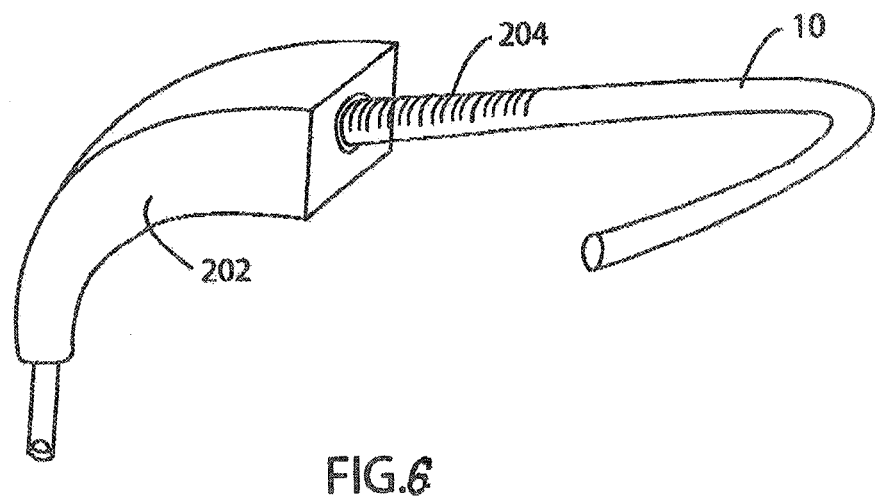
FIG. 6 shows the length marking 204 on a catheter 10 advanced through an oral intubation device 202

The tumor application for the devices described above takes advantage of the energy 1/r dispersion characteristics (significant depth without undue near field damage) as long as a coupling balloon is utilized. Once a lung tumor has been diagnosed with CT or MRI a guidewire is typically inserted under 3-dimensional guidance (i.e. Super Dimensions) in order to perform a biopsy. These systems combine 3D imaging with the localization of guidewires during bronchoscopy. However, treatment is typically performed later, in separate follow-up procedures. In the same biopsy procedure the guidewire may be used to advance the above-described ultrasound treatment catheter into the tumor. Depending on lesion volume, the ultrasound dose is calculated and one or more lesions are generated. Preferably, the ablation is performed under image guidance. In particular the annular array configuration of FIG. 5 provides image guidance of highest resolution which allows differentiation of tumor and normal tissues. In FIG. 5 a three element rotating annular array transducer 11" is shown. Another way to perform the tumor ablation, image guided, is to exchange treatment and imaging catheters over the guidewire. An IVUS imaging catheter may be advanced after withdrawal of the treatment catheter to monitor the tumor ablation progress and change back to the treatment catheter if the IVUS image shows non-ablated tumor regions. Catheter exchange is simplified with length markings 204 as shown in FIG. 6.

An additional application for the devices described above is reducing negative effects of ARDS caused by COVID 19 by optimizing utilization of the remaining healthy lung capacity by preventing or reducing bronchial contraction and mucus secretion through denervation at the secondary bronchi.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for performing pulmonary interventions in a mammalian subject, comprising:
   providing an ultrasound catheter having an ultrasound transducer at a distal end;
   inserting the ultrasound catheter into a bronchus of a bronchial system of the mammalian subject so that the ultrasound transducer is disposed proximate to a treatment site;
   while the ultrasound transducer is disposed proximate to the treatment site, operating an actuator or control unit electrically connected to the ultrasound transducer, to energize the ultrasound transducer to emit a short pulse at a sub-therapeutic level;
   receiving via the ultrasound transducer an ultrasound echo from organic tissues of the mammalian subject in response to the short pulse, the ultrasound echo being a volume-integrated A-mode signal;
   operating the actuator or control unit to process the volume integrated A-mode signal, which represents an accumulated intensity of the circumferential ultrasound echoes;
   analyzing the volume integrated A-mode signal to determine longitudinal locations of cartilage along the bronchus; and activating the ultrasound transducer to transmit ultrasound therapeutic waveform energy through the bronchus at longitudinal locations without cartilage, wherein the ultrasound transducer is disposed inside a balloon attached to the distal end of the ultrasound catheter, further comprising analyzing the volume integrated A-mode signal to detect presence of air pockets or trapped air between the balloon and surrounding tissue, the activating of the ultrasound transducer to transmit ultrasound therapeutic waveform energy being carried out only when analyzing of the volume integrated A-mode signal reveals an absence of air, thereby ensuring complete circumferential coupling.

2. A method for performing pulmonary interventions in a mammalian subject, comprising:

inserting an ultrasound transducer into a bronchus of the mammalian subject so that the ultrasound transducer is disposed proximate to a treatment site;

while the ultrasound transducer is disposed proximate to the treatment site, operating an actuator or control unit electrically connected to the ultrasound transducer, to energize the ultrasound transducer to emit a pulse at a sub-therapeutic level;

receiving, via the ultrasound transducer, ultrasound echoes from organic tissues of the mammalian subject in response to the pulse;

operating the ultrasound transducer to produce a volume-integrated A-mode signal representing an accumulated intensity of the ultrasound echoes;

operating the actuator or control unit to process and analyze the volume integrated A-mode signal to determine presence of cartilage along the bronchus;

activating the ultrasound transducer to transmit ultrasound therapeutic waveform energy through a wall of the bronchus at one or more locations along the bronchus determined by the analyzing of the volume integrated A-mode signal to be without cartilage; and wherein the ultrasound transducer is disposed inside a balloon, further comprising operating the actuator or control unit to analyze the volume integrated A-mode signal to detect presence of air pockets or trapped air between the balloon and surrounding tissue, the activating of the ultrasound transducer to transmit ultrasound therapeutic waveform energy being carried out only when analyzing of the volume integrated A-mode signal reveals an absence of air, thereby ensuring complete circumferential coupling.

3. The method of claim 2, wherein the activating of the ultrasound transducer includes longitudinally shifting the ultrasound transducer along the bronchus to position the ultrasound transducer at the one or more locations along the bronchus without cartilage.

4. The method of claim 2 wherein the ultrasound transducer includes a longitudinal array of separately activatable cylindrical transducer elements and the activating of the ultrasound transducer includes energizing a selected one of the separately activatable transducer elements to transmit the ultrasound therapeutic waveform energy through the wall of the bronchus at the one or more locations along the bronchus without cartilage.

5. The method of claim 2, further comprising operating the actuator or control unit to measure a time delay of the volume integrated A-mode signal and therewith determine size of a bronchial section, also comprising operating the actuator or control unit to control the ultrasound transducer to vary the amount of the therapeutically effective ultrasound energy in accordance with the determined size of the bronchial section taking into account catheter efficiency variations.

6. A method for performing pulmonary interventions in a mammalian subject, comprising:

providing an ultrasound transducer and a balloon;

inserting the ultrasound transducer and the balloon into a bronchus of the mammalian subject so that the ultrasound transducer and balloon are disposed proximate to a treatment site, with the ultrasound transducer inside the balloon;

while the ultrasound transducer and the balloon are disposed proximate to the treatment site, inflating the balloon with a liquid so that an outer surface of the balloon is in contact with the bronchus;

thereafter operating an actuator or control unit electrically connected to the ultrasound transducer, to energize the ultrasound transducer to emit a pulse at a sub-therapeutic level;

receiving, via the ultrasound transducer, ultrasound echoes from organic tissues of the mammalian subject in response to the pulse;

operating the ultrasound transducer to produce a volume-integrated A-mode signal representing an accumulated intensity of the ultrasound echoes;

analyzing the volume integrated A-mode signal to detect presence of air pockets or trapped air between the balloon and surrounding tissue; and activating the ultrasound transducer to transmit ultrasound therapeutic waveform energy into the surrounding tissue and to the treatment site only when analyzing of the volume integrated A-mode signal reveals an absence of air between the balloon and the bronchus, thereby ensuring complete circumferential coupling.

* * * * *